United States Patent
Adams (10) Patent No.: US 10,386,329 B2
(45) Date of Patent: Aug. 20, 2019

(54) DIGITAL CONTROLLER FOR AN OXYGEN SENSOR

(71) Applicant: AEM PERFORMANCE ELECTRONICS, Hawthorne, CA (US)

(72) Inventor: Michael Adams, Laguna Hills, CA (US)

(73) Assignee: AEM Performance Electronics, Hawthorne, CA (US)

(*) Notice: Subject to any disclaimer, the term of this patent is extended or adjusted under 35 U.S.C. 154(b) by 95 days.

(21) Appl. No.: 15/384,134

(22) Filed: Dec. 19, 2016

(65) Prior Publication Data
US 2017/0097318 A1 Apr. 6, 2017

Related U.S. Application Data

(63) Continuation of application No. 14/028,331, filed on Sep. 16, 2013, now Pat. No. 9,575,030.

(60) Provisional application No. 61/744,029, filed on Sep. 17, 2012.

(51) Int. Cl.
*G01N 27/41* (2006.01)
*G01N 27/416* (2006.01)

(52) U.S. Cl.
CPC ......... *G01N 27/4163* (2013.01); *G01N 27/41* (2013.01)

(58) Field of Classification Search
CPC ............. G01N 27/41–4163; G01N 27/406–41
See application file for complete search history.

(56) References Cited

U.S. PATENT DOCUMENTS

| 6,177,001 | B1  |   1/2001 | Meyer |
| 6,301,951 | B1  |  10/2001 | Lenfers et al. |
| 6,383,354 | B1* |   5/2002 | Kurokawa ......... G01N 27/4074 204/406 |
| 2001/0020587 | A1 | 9/2001 | Amtmann et al. |
| 2005/0000810 | A1 | 1/2005 | Tashiro et al. |
| 2005/0133381 | A1 | 6/2005 | Kerns et al. |
| 2006/0027012 | A1 | 9/2006 | Allmendinger |
| 2007/0108053 | A1 | 5/2007 | Cramer et al. |
| 2007/0119435 | A1 | 5/2007 | Carter et al. |
| 2009/0173326 | A1 | 7/2009 | Aoki |

* cited by examiner

*Primary Examiner* — J. Christopher Ball
(74) *Attorney, Agent, or Firm* — Rutan & Tucker LLP; Hani Z. Sayed (57) ABSTRACT

An apparatus and method are provided for digitally controlling an oxygen sensor. The apparatus comprises a computer and digital circuitry coupled to the oxygen sensor to convey information between the oxygen sensor and the computer. The oxygen sensor includes a pump cell and at least one Nernst cell configured to indicate the difference in oxygen content in a test medium relative to a reference medium. A pump control circuit operates the pump cell according to signals received from the computer based on output signals from the Nernst cell. A reference voltage circuit enables the computer to determine impedances of the oxygen sensor as a function of sensor temperature and pressure. A Nernst read circuit transmits output signals from the oxygen sensor digitally to the computer. Digital signals received by the computer are compared with stored reference information so as to determine the oxygen content of the test medium.

30 Claims, 5 Drawing Sheets

DIGITAL CONTROLLER FOR AN OXYGEN SENSOR

RELATED APPLICATION

This continuation application claims the benefit of and priority to U.S. patent application Ser. No. 14/028,331 filed on Sep. 16, 2013, entitled "Digital Controller For An Oxygen Sensor" and U.S. Provisional Application No. 61/744,029 filed on Sep. 17, 2012, entitled "Method of Control and Read a Wide Band Oxygen Sensor."

FIELD OF THE INVENTION

The present invention generally relates to operating sensors. More particularly, the invention relates to an apparatus and method for digitally controlling and reading a wideband oxygen sensor.

BACKGROUND

An oxygen sensor generally measures an oxygen concentration of a test medium, such as exhaust gases of an internal combustion engine, relative to a reference medium, such as the atmosphere. Oxygen sensors find applicability in a wide variety of areas, such as, by way of example, automotive applications, oxygen analyzers and ppO$_2$ meters for determining oxygen concentrations of breathing gas mixtures utilized in scuba gear, soil oxygen sensors utilized in soil respiration studies, electrochemical sensors and optical sensors frequently used in marine biology or limnology oxygen measurements, and other similar types of oxygen sensors.

Oxygen sensors utilized with internal combustion engines are commonly available as either narrowband sensors or wideband sensors. A narrowband oxygen sensor comprises a single measurement cell, called a "Nernst cell," which produces an output voltage that is dependent upon a difference in concentration of free oxygen in a test medium, such as exhaust gas of an internal combustion engine, and a reference medium such as the surrounding atmosphere. The concentration of oxygen in the atmosphere is approximately 20.8%, whereas the concentration of oxygen in exhaust gas is 0% when the engine is operating at stoichiometric conditions. Thus, the difference in oxygen concentration is 20.8%, and the narrowband Nernst cell consequently produces a voltage of approximately 450 millivolts (mV). As the difference in oxygen concentration deviates from 20.8%, however, the Nernst cell produces disproportionate output voltages that are not indicative of the actual oxygen concentration differential. Therefore, narrowband oxygen sensors are not suitable for use with internal combustion engines operating outside of stoichiometric conditions.

A wideband oxygen sensor typically comprises a Nernst cell and a pump cell enclosed within a shared volume. The pump cell is an electrochemical device which selectively pumps free oxygen within the test medium into and out of the shared volume in direct proportion to an electric current directed to the pump. During operation, a wideband oxygen sensor controller uses the pump cell to maintain a stable oxygen concentration within the shared volume such that the Nernst cell produces a steady output voltage of 450 mV, which indicates a 0% oxygen concentration in the exhaust gas. The amount of current that must be supplied to the pump cell and the output voltage of the Nernst cell indicate the actual concentration of oxygen in the exhaust gas relative to the surrounding atmosphere.

Existing wideband oxygen sensor systems utilize an analog control circuit to control the current directed to the pump cell. An inherent difficulty with such systems is that the Nernst cell and the pump cell have internal resistances that are temperature dependent. The temperature of the oxygen sensor must be maintained to keep the internal resistances of the Nernst cell and the pump cell at constant values specified by the manufacturer. Thus, a method of measuring the internal resistances within the oxygen sensor must be employed. Typically, an alternating current (AC) signal is directed through a resistor having a known value, and the resultant attenuation of the AC signal is measured to determine the internal resistance of the Nernst cell. Although the AC signal approach leads to reasonably accurate measurements, the AC signal has a tendency to create oscillations within the analog control circuit, causing it to become unstable. Consequently, the Nernst cell signal must be processed by a low-pass filtering circuit to remove the AC signal and enable the analog feedback loop to operate properly.

A drawback to filtering the Nernst cell signal is that it slows down the entire system. This slowing down of the system is so severe that the system cannot resolve transitioning concentrations of oxygen in exhaust gases, such as during vehicle acceleration, deceleration, and other engine-load changes. While the wideband oxygen sensor is perfectly capable of resolving transitioning concentrations of oxygen, the analog control circuit and filtering circuitry renders the sensor useless except under steady states of engine operation. What is needed, therefore, is a discrete-time, digital controller for an oxygen sensor which accurately resolves oxygen concentrations of exhaust gases during transitioning concentration states, as well as steady states.

SUMMARY

The present invention provides a method and apparatus for a digital controller of a wideband oxygen sensor for detecting a difference in oxygen concentration in a test medium relative to a reference medium. The test medium preferably is exhaust gases from an internal combustion engine, and the reference medium may be a sealed gas charge, the surrounding atmosphere, or other functional equivalent. A computer is configured to send and receive digital signals so as to communicate with and operate circuitry comprising the digital controller. The computer further includes stored reference information including, but not necessarily limited to, tables, formulae, sensor temperature data, sensor pressure data, and the like, to facilitate regulating the operation of the oxygen sensor and determining the oxygen concentration of the test medium. The oxygen sensor comprises at least one Nernst cell and a pump cell. A pump control circuit in operative communication with the computer and the pump cell enables the computer to control the amount of electric current directed to the pump cell, such that the signals received from the Nernst cell indicate a steady voltage of 450 mV. Signals from the Nernst cell are transmitted to the computer by way of amplifiers that pass the signals to sample-and-hold circuits. Each sample-and-hold circuit comprises at least one capacitor and a switch in operative communication with the computer through an analog-to-digital converter. The computer operates each switch such that an output voltage of the signal amplifier is passed to the capacitor and subsequently transmitted to the analog-to-digital converter for interpretation by the computer.

A reference voltage circuit facilitates determining a real-time, temperature dependent impedance of the Nernst cell by performing measurements of output signals received from the Nernst cell. The computer uses differences in the output signals of the Nernst cell with the reference voltage circuit activated and deactivated to determine the real-time impedance of the Nernst cell. Once resolved, the impedance of the Nernst cell may be used to regulate the operating temperature of the oxygen sensor. Moreover, the impedance of the Nernst cell may be used in conjunction with an impedance of the pump cell and an impedance of the common terminal of the oxygen sensor to establish a relationship between pressure of the test medium acting on the oxygen sensor and the temperature of the oxygen sensor. The impedances of the Nernst cell and the pump cell are sensitive to both temperature and pressure, whereas the impedance of the sensor's common terminal is sensitive to only temperature. Once the relationship between temperature and pressure is determined, the temperature of the oxygen sensor may be advantageously regulated by measuring the impedance of the sensor's common terminal. Regulating the temperature of the oxygen sensor by way of the impedance of the sensor's common terminal is advantageous in systems comprising variable pressure, such as turbocharged engine systems, where the variable pressure would otherwise cause erroneous output signals from the Nernst cell.

To this end in an exemplary embodiment, a digital controller for an oxygen sensor is provided.

In an exemplary embodiment, an apparatus for detecting a difference in oxygen content in a test medium relative to a reference medium, comprising: a computer configured to send and receive digital signals so as to communicate with and operate circuitry comprising said apparatus; an oxygen sensor comprising at least one Nernst cell and a pump cell, wherein the oxygen sensor is configured to electrically indicate the difference in oxygen content in the test medium relative to the reference medium; a pump control circuit configured to operate the pump cell according to signals received from the computer; a reference voltage circuit configured to determine an impedance of the oxygen sensor according to signals received from the computer; and a Nernst read circuit configured to amplify output signals from the oxygen sensor and transmit the signals digitally to the computer, wherein the signals received by the computer are compared with stored reference information to determine the oxygen content of the test medium.

In another exemplary embodiment, wherein the test medium is exhaust gases from an internal combustion engine.

In another exemplary embodiment, wherein the reference medium is a sealed gas charge, surrounding atmospheric air, or a functional equivalent.

In another exemplary embodiment, wherein a first terminal of the oxygen sensor is electrically connected to the Nernst cell, a second terminal of the oxygen sensor is electrically connected to the pump cell, and a third terminal of the oxygen sensor is electrically common to both the Nernst cell and the pump cell.

In another exemplary embodiment, wherein the pump control circuit further comprises a digital-to-analog converter in operative communication with the computer, a reference voltage source, and a voltage controlled current source, where the reference voltage source is electrically connected to the second terminal and the voltage controlled current source, and the voltage controlled current source is electrically connected to the third electrical terminal.

In another exemplary embodiment, wherein the reference voltage circuit further comprises a reference voltage source, a switch in operative communication with the computer, and a known Nernst cell test resistance, where the known Nernst cell test resistance is connected to the first electrical terminal of the oxygen sensor.

In another exemplary embodiment, wherein the Nernst read circuit is in operative communication with the computer through at least one analog-to-digital converter.

In another exemplary embodiment, wherein at least one switch is operated by the computer such that an output voltage signal of the Nernst cell is passed to the at least one analog-to-digital converter and interpreted by the computer.

In another exemplary embodiment, wherein said computer further includes stored reference information to determine the oxygen content of the test medium based on signals received from the Nernst read circuit.

In another exemplary embodiment, wherein the impedance of the oxygen sensor varies in proportion to temperature.

In an exemplary embodiment, an apparatus for detecting a difference in oxygen content in a test medium relative to a reference medium, comprising: a computer configured to send and receive digital signals so as to communicate with and operate circuitry comprising said apparatus, wherein said computer further includes stored reference information to determine the oxygen content of the test medium; an oxygen sensor comprising at least one Nernst cell and a pump cell, wherein a first terminal of the oxygen sensor is electrically connected to the Nernst cell, a second terminal of the oxygen sensor is electrically connected to the pump cell, and a third terminal of the oxygen sensor is electrically common to both the Nernst cell and the pump cell; a pump control circuit comprising a digital-to-analog converter in operative communication with the computer, a reference voltage source, and a voltage controlled current source, where the reference voltage source is electrically connected to the second terminal and the voltage controlled current source, and the voltage controlled current source is electrically connected to the third electrical terminal; a reference voltage circuit comprising a reference voltage source, a switch in operative communication with the computer, and a known Nernst cell test resistance, where the known Nernst cell test resistance is connected to the first electrical terminal of the oxygen sensor; and a Nernst read circuit comprising at least one analog-to-digital converter in operative communication with the at least one Nernst cell and the computer.

In another exemplary embodiment, wherein at least one switch is operated by the computer such that an output voltage signal of the Nernst cell is passed to the at least one analog-to-digital converter and interpreted by the computer.

In another exemplary embodiment, wherein the test medium is exhaust gases from an internal combustion engine.

In another exemplary embodiment, wherein the reference medium is a sealed gas charge, surrounding atmospheric air, or a functional equivalent.

In an exemplary embodiment, a method for detecting a difference in oxygen content in a test medium relative to a reference medium, comprising: configuring a computer to send and receive digital signals so as to communicate with and operate circuitry suitable for detecting the difference in oxygen content in the test medium relative to the reference medium; using an oxygen sensor comprising at least one Nernst cell, a pump cell, and a heating element to electrically indicate the difference in oxygen content in the test medium relative to the reference medium, wherein a first terminal is electrically connected to the Nernst cell, a second terminal is electrically connected to the pump cell, and a third terminal of the oxygen sensor is electrically common to both the Nernst cell and the pump cell; operating the pump cell according to signals received from the Nernst cell; determining a real-time impedance of the Nernst cell; determining a real-time impedance of the third terminal of the oxygen sensor; determining a pressure of the test medium acting on the oxygen sensor; regulating a temperature of the oxygen sensor; transmitting output signals from the Nernst cell digitally to the computer; and comparing the output signals received from the Nernst cell with stored reference information to determine the oxygen content of the test medium.

In another exemplary embodiment, wherein operating the pump cell further comprises using a reference voltage source to maintain the second terminal at a constant reference voltage, and using a digital-to-analog converter in communication with the computer to operate a voltage controlled current source, where the voltage controlled current source directs an electric current to the third electrical terminal of the oxygen sensor according to the output signals received from the Nernst cell.

In another exemplary embodiment, wherein operating the pump cell further comprises varying the electric current directed to the third electrical terminal such that the output signals received from the Nernst cell indicate a steady voltage of 450 mV.

In another exemplary embodiment, wherein determining a real-time impedance of the Nernst cell comprises performing at least a first measurement and a second measurement of the output signals received from the Nernst cell at the first terminal, wherein the first measurement is performed while directing zero electric current to the third terminal and the second measurement is performed while using a reference voltage circuit to apply a known reference voltage to a known Nernst cell test resistance, and using the difference between the first measurement and the second measurement in conjunction with the known reference voltage and the known Nernst cell test resistance to resolve the real-time impedance of the Nernst cell.

In another exemplary embodiment, further comprising successively performing the first measurement and the second measurement whenever zero electric current is directed to the third terminal, where the known reference voltage is decoupled through a capacitor after each of the second measurements such that the Nernst cell indicates a steady output voltage.

In another exemplary embodiment, wherein determining a real-time impedance of the third terminal of the oxygen sensor comprises measuring electric signals in the first terminal, the second terminal, and the third terminal, and discerning the real-time impedance of the third terminal based on relative amplitudes of the electric signals.

In another exemplary embodiment, wherein determining a pressure of the test medium acting on the oxygen sensor comprises establishing a relationship between the real-time impedance of the third terminal of the oxygen sensor with the real-time impedance of the Nernst cell and a real-time impedance of the pump cell, wherein the impedance of the Nernst cell and the impedance of the pump cell change in proportion to the temperature of the oxygen sensor and the pressure of the test medium, and wherein the impedance of the third terminal of the oxygen sensor is insensitive to the pressure of the test medium.

In another exemplary embodiment, wherein transmitting output signals comprises passing an output voltage of the Nernst cell to the at least one analog-to-digital converter for interpretation by the computer.

In another exemplary embodiment, wherein the test medium is exhaust gases from an internal combustion engine.

In another exemplary embodiment, wherein the reference medium is a sealed gas charge, surrounding atmospheric air, or a functional equivalent.

In another exemplary embodiment, wherein regulating the temperature comprises: measuring a voltage contribution of the pump cell arising between the first terminal and the third terminal; determining a pump cell impedance in accordance with the voltage contribution and the electric current directed to the pump cell; deducing a real-time temperature of the oxygen sensor by comparing the pump cell impedance with known impedance values, wherein the pump cell impedance changes in proportion to the temperature of the oxygen sensor; and modulating an electric current directed to the heating element such that a comparison of the pump cell impedance and the known impedance values indicates an appropriate operating temperature of the oxygen sensor.

In an exemplary embodiment, an apparatus for detecting a difference in oxygen content in a test medium relative to a reference medium, comprising: a computer configured to send and receive digital signals so as to communicate with and operate circuitry comprising said apparatus; an oxygen sensor comprising at least one Nernst cell, a pump cell, and a heating element, wherein the oxygen sensor is configured to electrically indicate the difference in oxygen content in the test medium relative to the reference medium; a pump control circuit configured to operate the pump cell according to signals received from the computer; a temperature control circuit configured to regulate an operating temperature of the oxygen sensor according to signals received from the computer; and a Nernst read circuit, comprising at least one analog-to-digital converter, configured to transmit output signals from the oxygen sensor digitally to the computer, wherein the signals received by the computer are compared with stored reference information to determine the oxygen content of the test medium.

In another exemplary embodiment, wherein a first terminal of the oxygen sensor is electrically connected to the Nernst cell, a second terminal of the oxygen sensor is electrically connected to the pump cell, a third terminal of the oxygen sensor is electrically common to both the Nernst cell and the pump cell, a fourth terminal of the oxygen sensor is electrically connected to a first input of the heating element, and a fifth terminal of the oxygen sensor is electrically connected to a second input of the heating element.

In another exemplary embodiment, wherein the pump control circuit further comprises a digital-to-analog converter in operative communication with the computer, a reference voltage source, and a voltage controlled current source, where the reference voltage source is electrically connected to the second terminal and the voltage controlled current source, and the voltage controlled current source is electrically connected to the third electrical terminal.

In another exemplary embodiment, wherein the temperature control circuit further comprises a heater power control in operative communication with the computer, wherein the heater power control is connected to the fourth terminal and the fifth terminal of the oxygen sensor.

In another exemplary embodiment, wherein the heater power control is configured to regulate the temperature of the oxygen sensor by directing a current to the heating element according to signals received from the computer.

In an exemplary embodiment, a method for regulating an operating temperature of a digitally controlled oxygen sensor, comprising: measuring a voltage contribution of a pump cell of the oxygen sensor arising between a first terminal and a second terminal of a Nernst cell of the oxygen sensor; determining a pump cell impedance in accordance with the voltage contribution and an electric current directed to the pump cell; deducing a real-time temperature of the oxygen sensor by comparing the pump cell impedance with known impedance values, wherein the pump cell impedance changes in proportion to the temperature of the oxygen sensor; and modulating an electric current directed to a heating element of the oxygen sensor such that a comparison of the pump cell impedance and the known impedance values indicates an appropriate operating temperature of the oxygen sensor.

BRIEF DESCRIPTION OF THE DRAWINGS

The drawings refer to embodiments of the present invention in which.

While the invention is subject to various modifications and alternative forms, specific embodiments thereof have been shown by way of example in the drawings and will herein be described in detail. The invention should be understood to not be limited to the particular foul's disclosed, but on the contrary, the intention is to cover all modifications, equivalents, and alternatives falling within the spirit and scope of the invention.

DETAILED DISCUSSION

In the following description, numerous specific details are set forth in order to provide a thorough understanding of the present invention. It will be apparent, however, to one of ordinary skill in the art that the present invention may be practiced without these specific details. Further specific numeric references such as a "first amplifier," may be made. However, the specific numeric references should not be interpreted as a literal sequential order but rather interpreted that the "first amplifier" is different than a "second amplifier." Thus, the specific details set forth are merely exemplary. The specific details may be varied from and still be contemplated to be within the spirit and scope of the present invention.

In general, an apparatus and method are provided for a digital controller for an oxygen sensor to detect a difference in oxygen content in a test medium relative to a reference medium. The digital controller comprises a computer, an oxygen sensor, and circuitry to convey information between the oxygen sensor and the computer. The computer is configured to send and receive digital signals so as to communicate with and operate the circuitry comprising the digital controller. The oxygen sensor includes a pump cell and at least one Nernst cell configured to electrically indicate the difference in oxygen content in the test medium relative to the reference medium. A pump control circuit operates the pump cell according to signals received from the computer based on output signals from the Nernst cell. A reference voltage circuit enables the computer to determine a temperature dependent impedance of the oxygen sensor so as to regulate operation of the oxygen sensor. A Nernst read circuit transmits output signals from the oxygen sensor digitally to the computer. The digital signals received by the computer are compared with stored reference information so as to determine the oxygen content of the test medium.

Figure 1:
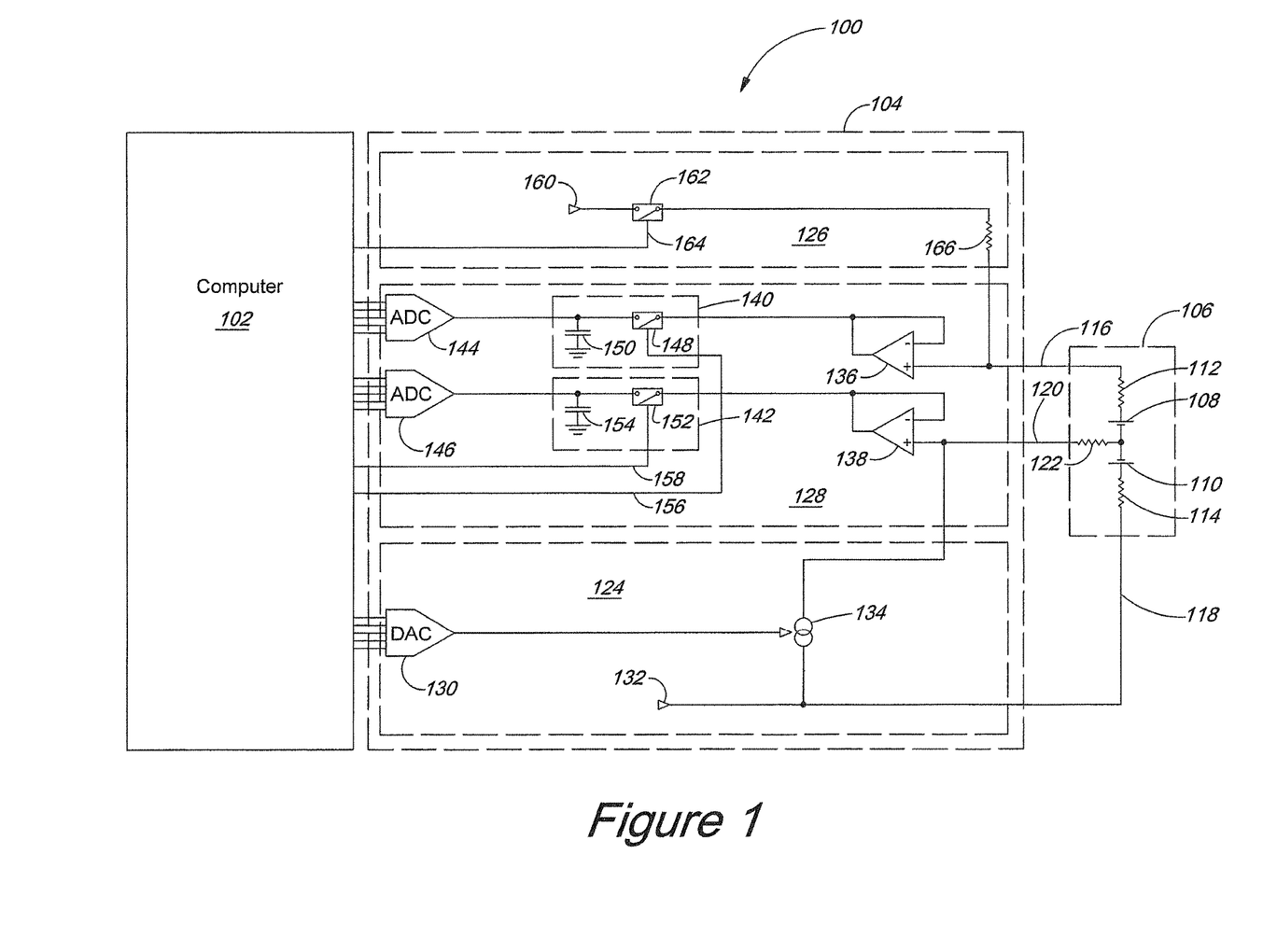
FIG. 1 is a schematic illustration of a digital controller for an oxygen sensor of the present invention.

FIG. 1 is a schematic illustration of a digital controller 100 for an oxygen sensor 106. In the embodiment illustrated in FIG. 1, the digital controller 100 comprises a computer 102 and a digital control circuit 104 coupled to the oxygen sensor 106. The computer 102 is configured to send and receive digital signals so as to operate the digital control circuit 104 and the oxygen sensor 106. In one embodiment, the computer 102 comprises a Digital Signal Processing (DSP) system, which is configured to sample incoming signals at a sample-frequency suitable to resolve data conveyed by the digital control circuit 104. The computer 102 also includes stored reference information to determine the oxygen content of the test medium, as well as to perform other critical functions such as, but not necessarily limited to, regulating an operating temperature of the oxygen sensor 106, measuring an internal impedance of the oxygen sensor, and compensating for pressure of the test medium acting on the oxygen sensor 106. The stored reference information may comprise tables, formulae, sensor temperature data, sensor pressure data, and the like.

It will be appreciated by one of ordinary skill in the art that a primary application of the digital controller 100 is with a wideband oxygen sensor typically used in an exhaust system of an internal combustion engine, wherein the test medium is exhaust gases from the engine, and the reference medium may be a sealed gas charge, the surrounding atmosphere, or other functional equivalent. However, the digital controller 100 may be coupled with other types of oxygen sensors that are used with mediums other than exhaust gases, such as, by way of example, oxygen analyzers and $ppO_2$ meters for determining oxygen concentrations of breathing gas mixtures utilized in scuba gear, soil oxygen sensors utilized in soil respiration studies, electrochemical sensors and optical sensors frequently used in marine biology or limnology oxygen measurements, and other similar types of oxygen sensors.

In the embodiment illustrated in FIG. 1, the oxygen sensor 106 comprises at least one Nernst cell 108 and a pump cell 110. The Nernst cell 108 has an internal impedance 112, and the pump cell 110 has an internal impedance 114. The oxygen sensor 106 further comprises a first terminal 116, a second terminal 118, and a third terminal 120. The first terminal 116 is electrically connected to the Nernst cell 108, the second terminal 118 is electrically connected to the pump cell 110, and the third terminal 120 of the oxygen sensor 106 is electrically common to both the Nernst cell 108 and the pump cell 110. The third terminal 120 has an internal impedance 122, as well. In one embodiment, the oxygen sensor 106 may be operated by using the pump cell 110 to move oxygen within the test medium into and out of a container (not shown) which houses the Nernst cell 108 and the pump cell 110. In another embodiment, the container which houses the Nernst cell 108 and the pump cell 110 may be sealed from the surrounding atmosphere and may include a chamber which contains the reference medium in the form of a gas charge. It will be appreciated by those skilled in the art that various configurations of the oxygen sensor 106 may be coupled with the digital control circuit 104 without deviating from the scope of the present invention.

During normal operation of the oxygen sensor 106, the pump cell 110 maintains an oxygen concentration within the container such that the Nernst cell 108 produces a stable output voltage of substantially 450 millivolts (mV), which corresponds to a 0% oxygen concentration in the test medium. The oxygen concentration of the test medium can be deduced based on the amount of electric current that must be supplied to the pump cell 110 to maintain the 450 mV output voltage of the Nernst cell 108. In an alternative embodiment, the Nernst cell 108 may be omitted from the oxygen sensor 106. Experimentation has demonstrated that the pump cell 110 responds to the oxygen content of the test medium in a manner substantially identical to the Nernst cell 108; that is, the pump cell 110 produces an offset voltage of substantially 450 mV in response to a 0% oxygen concentration in the test medium. Thus, this embodiment of the oxygen sensor 106 enables determination of the oxygen content of the test medium solely by way of the pump cell 110. It will be recognized that using the pump cell 110 alone to detect oxygen concentrations reduces the response time of the digital control circuit 104, which is advantageous in systems wherein the oxygen content is in transition, such as during engine load-changes due to vehicle acceleration, deceleration, gear transitions, and the like.

As shown in FIG. 1, the digital control circuit 104 comprises a pump control circuit 124, a reference voltage circuit 126, and a Nernst read circuit 128. The pump control circuit 124 comprises a digital-to-analog converter (DAC) 130 in operative communication with the computer 102, a reference voltage source 132, and a voltage controlled current source 134. The reference voltage source 132 is electrically connected to the second terminal 118 of the oxygen sensor 106, and the voltage controlled current source 134 is electrically connected to the third terminal 120 as well as to the reference voltage source 132.

Figure 2A:
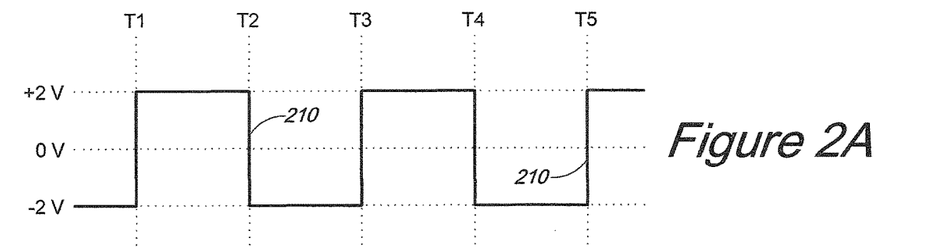
FIG. 2A illustrates one embodiment of a voltage signal transmitted from a digital-to-analog converter to a voltage controlled current source of the present invention.

During operation of the digital controller 100, the computer 102 prompts the DAC 130 to output a voltage signal to the voltage controlled current source 134. FIG. 2A illustrates one embodiment of a voltage signal 210 that is transmitted by the DAC 130 at switch times T1-T5 during operation of the digital controller 100. The voltage signal 210 changes from a negative polarity to a positive polarity at switch time T1, remains constant between switch times T1 and T2, and then switches back to the negative polarity at switch time T2. At switch time T3, the voltage signal 210 changes to the positive polarity, remains constant until switch time T4, at which time the voltage signal 210 changes back to the negative polarity. The voltage controlled current source 134 responds to the output voltage signal 210 of the DAC 130 by directing an electric current to the third terminal 120 of the oxygen sensor 106. The reference voltage 132 simultaneously maintains the second terminal 118 at a constant reference voltage. In one embodiment, the reference voltage 132 may be connected to an electrical ground of the digital control circuit 104. In other embodiments, the reference voltage 132 may be a suitable voltage other than the electrical ground. The current output of the voltage controlled current source 134 and the reference voltage 132 together direct a voltage controlled electric current 215 to the pump cell 110.

Figure 2B:
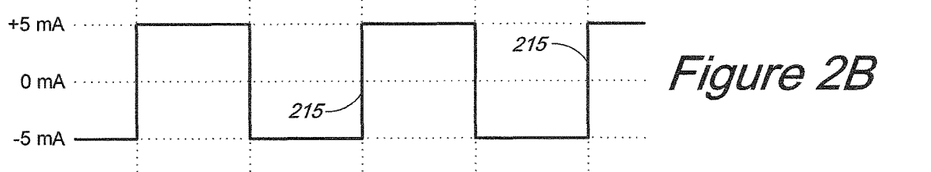
FIG. 2B is a graph illustrating an embodiment of a voltage controlled electric current directed to a pump cell of the present invention.
Figure 2C:
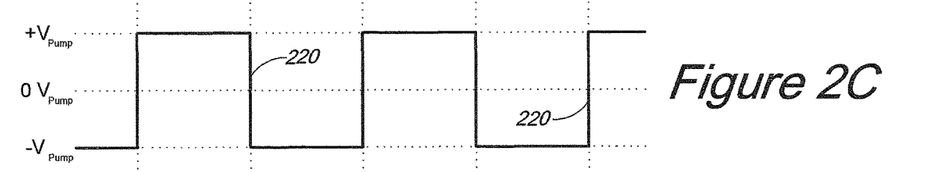
FIG. 2C is a graph illustrating an embodiment of a voltage signal at the pump cell in accordance with the present invention.

FIG. 2B is a graph illustrating one embodiment of the voltage controlled electric current 215 directed to the pump cell 110. FIG. 2C is a graph illustrating one embodiment of a voltage signal 220 at the pump cell 110. The electric current 215 directed to the pump cell 110 changes from a negative current to a positive current at switch time T1, remains at a constant positive value between switch times T1 and T2, and then becomes negative at switch time T2. At switch time T3, the electric current 215 becomes positive again, then remains constant until switch time T4, and then returns to the negative value. As illustrated in FIG. 2C, the voltage signal 220 applied to the pump cell 110 follows a similar pattern. At the switch time T1, the voltage signal 220 changes from a constant negative polarity to a constant positive polarity. The polarity remains constant between the switch times T1 and T2, and then assumes a negative polarity between the switch times T2 and T3. The polarity returns to the positive value between T3 and T4, and then becomes negative again between T4 and T5.

It should be recognized that the amplitudes and polarities of the illustrated signals, as well as the timing and duration between the switch times T1-T5, are not limited to the specific values shown in FIGS. 2A-2E, but rather the signals and the switch times are controlled by the computer 102, and thus other values can be used without deviating from the scope of the present invention. It should be further recognized that the total number of the switch times is not limited to that shown in FIGS. 2A-2E, rather the total number of switch times is directly proportional to the duration with which the signals shown are allowed to continue operating, and thus any number of the switch times may be possible. Moreover, those of ordinary skill in the art will recognize that the duration, amplitude, and polarity of the signals may be modulated intelligently (e.g., Pulse Width Modulation (PWM)) so as to direct a specific degree of power to the pump cell 110. In one embodiment, the electric current 215 directed to the pump cell 110 is modulated with a frequency ranging between 1 kiloHertz (kHz) and 4 kHz. It will be appreciated that with a high enough frequency of the switch times, the alternating character of the signals shown in FIGS. 2A-2C will advantageously resemble constant, steady-state signals. Therefore, PWM may be used such that alternating current (AC) signals resemble direct current (DC) signals, possessing a voltage and a current suitable to efficiently operate the pump cell 110 without straying beyond the spirit of the present invention.

Figure 2D:
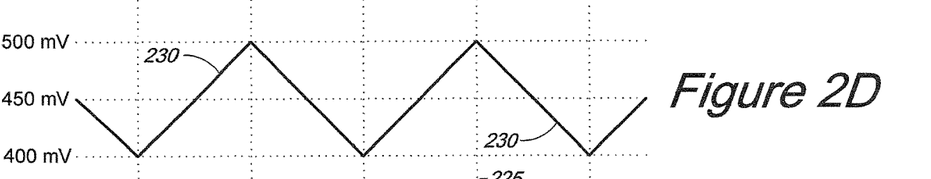
FIG. 2D is a graph illustrating one embodiment of an output signal produced by a Nernst cell in accordance with the present invention.

Those skilled in the art will appreciate that the computer 102 and the DAC 130 are capable of operating the pump cell 110 in a forward as well as a reverse direction, depending upon the direction of the voltage controlled electric current 215 directed to the pump cell 110, and thereby moving oxygen within the test medium respectively into and out of the container (not shown) which houses the Nernst cell 108 and the pump cell 110. It will be further appreciated that varying the signals within the pump control circuit 124, as illustrated in FIGS. 2A-2C, correspondingly varies the concentration of oxygen to which the Nernst cell 108 is exposed, and consequently varies an output signal from the Nernst cell 108. FIG. 2D is a graph illustrating one embodiment of the output voltage signal 230 produced by the Nernst cell 108 in the embodiment of FIG. 1. As shown in FIG. 2D, the output voltage signal 230 produced by the Nernst cell 108 alternates uniformly between 400 mV and 500 mV, which may be interpreted to be a steady, or average, output voltage of substantially 450 mV. It should be appreciated that in other embodiments, the signals within the pump control circuit 124 may be varied differently than as shown in FIGS. 2A-2C, thus giving rise to an output voltage signal 230 from the Nernst cell 108 that is different than illustrated in FIG. 2D without deviating from the scope of the present invention.

Figure 2E:
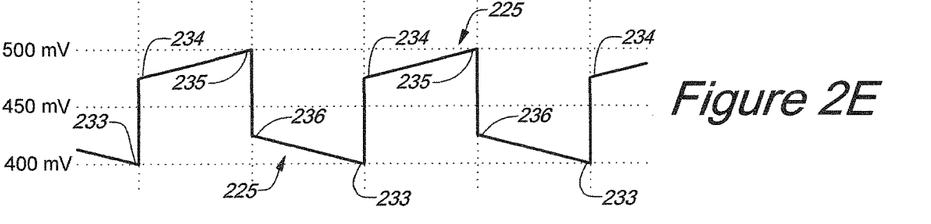
FIG. 2E is a graph illustrating one embodiment of an output signal transmitted from an oxygen sensor to a Nernst read circuit of the present invention.

FIG. 2E is a graph illustrating one embodiment of an output signal 225 which is transmitted from the oxygen sensor 106 to the Nernst read circuit 128 by way of the first terminal 116 and the third terminal 120. It will be appreciated that the output signal 225 represents a sum of the signals produced by the Nernst cell 108, the reference voltage source 132, and the pump cell 110, as well as including the effects of the impedances 112, 114, and 122. In the embodiment illustrated in FIG. 1, the Nernst read circuit 128 comprises at least a first signal amplifier 136 and a second signal amplifier 138. The first signal amplifier 136 is electrically connected to a sample-and-hold circuit 140, while the second signal amplifier 138 is connected to a sample-and-hold circuit 142. Each of the sample-and-hold circuits 140, 142 is in operative communication with the computer 102 through respective analog-to-digital converters (ADC) 144, 146. Moreover, the sample-and-hold circuit 140 is comprised of a switch 148 and a grounded capacitor 150. Similarly, the sample-and-hold circuit 142 is comprised of a switch 152 and a grounded capacitor 154. Each of the switches 148, 152 may be operated by the computer 102 by way of respective electrical connections 156, 158. In the illustrated embodiment, the signal amplifiers 136, 138, the sample-and-hold circuits 140, 142, the ADCs 144, 146, as well as the electrical connections 156, 158 are separate components. In other embodiments, however, various components of the Nernst read circuit 128 may be advantageously combined. For instance, the electrical connections 156, 158 may be incorporated into the ADCs 144, 146 without deviating from the scope of the present invention.

During operation, the output signal 225 is transmitted from the oxygen sensor 106 to the signal amplifiers 136, 138. The signal amplifiers 136, 138 serve to isolate the output signal 225 from interference effects, or "noise," arising within other portions of the digital control circuit 104. The signal amplifiers 136, 138 preferably have a gain value of substantially 1:1; however, other suitable values of the gain will be apparent to those skilled in the art. The outputs of the signal amplifiers 136, 138 are then transmitted to the computer 102 by way of the sample-and-hold circuits 140, 142 and the ADCs 144, 146. The switches 148, 152 and the grounded capacitors 150, 154 enable the computer 102 to control the frequency and amount of time during which measurements of the output signal 225 are performed.

In the illustrated embodiment of FIG. 2E, the computer 102 performs voltage measurements 233, 234, 235, and 236 of the output signal 225. Voltage measurement 233 is performed immediately prior to the switch time T1, at which point the electric current 215 directed to the pump cell 110 is negative. Voltage measurement 234 is performed immediately after the switch time T1 when the electric current 215 has assumed a constant, positive value. Voltage measurement 235 is performed just prior to the switch time T2, and voltage measurement 236 is performed immediately after the switch time T2 when the electric current 215 has assumed a constant, negative value. It should be understood that the number of the voltage measurements performed by the computer 102 is not limited to the number shown in FIG. 2E. Rather, the voltage measurements 233, 234, 235, and 236 are representative of a spectrum of similar measurements continually performed by the computer 102 for as long as the digital controller 100 is operating.

In the illustrated embodiment of FIGS. 2A-2E, the signals are waveforms all having the same wavelength and frequency. In one embodiment, the signals have a frequency of 1 kHz. Thus, the waveforms have a period of 0.001 seconds. It will be appreciated that the degree to which the output signal 225 may be characterized depends on how many samples (e.g., the voltage measurements 233, 234, 235, and 236) are performed within each 0.001-second interval of time. In one embodiment, a 1% accuracy may be achieved by performing substantially 400,000 samples per second. In another embodiment, an accuracy of substantially 0.06% may be achieved by performing 16,000,000 samples per second.

In the exemplary embodiment of FIG. 1, however, the computer 102 establishes the waveforms illustrated in FIGS. 2A-2C. Consequently, the computer 102 may time the voltage measurements 233, 234, 235, and 236 to occur at those advantageous locations along the output signal 225 that are illustrated in FIG. 2E. Those skilled in the art will recognize that the computer 102 timing the voltage measurements 233, 234, 235, and 236 according to the waveforms generated by the computer 102 reduces the number of samples that must be performed, thereby eliminating any need for selecting quality data from among millions of performed samples. In the embodiment illustrated in FIGS. 1-2E, an accuracy of 0.06% is achieved by performing substantially 4,000 of the voltage measurements 233, 234, 235, and 236 per second.

The voltage measurements 233, 234, 235, and 236 used in conjunction with the known value of the electric current 215 and the switch times T1-T5 enable the computer 102 to derive various operating characteristics of the Nernst cell 108, and thereby manage the performance of the oxygen sensor 106. For example, the computer 102 may calculate an average value of the voltage measurements 233, 234, 235, and 236 to determine an average output voltage of the Nernst cell 108, as discussed with reference to FIG. 2D. Determining the average output voltage of the Nernst cell 108 enables the computer 102 to make changes to the voltage controlled electric current 215 directed to the pump cell 110, as discussed with reference to FIG. 2C, so as to maintain the average voltage of the Nernst cell 108 at substantially 450 mV.

It will be apparent to those skilled in the art that a crucial performance parameter to determine is an average current flow occurring over one duty cycle. The computer 102 may determine the duty cycle by calculating a first difference, T2-T1, and a second difference, T3-T1, and then dividing the first difference by the second difference. Next, the computer 102 may determine the average current flow by calculating the product of the duty cycle and the voltage controlled electric current 215 directed to the pump cell 110. Once the value of the average current flow is determined, the computer 102 may compare the value with stored tables, formulae, or other similar data supplied by a manufacturer of the oxygen sensor 106, thereby enabling the computer 102 to determine the oxygen content of the test medium.

Those skilled in the art will recognize that the impedances 112, 114, and 122 vary as a function of an operating temperature of the oxygen sensor 106, as well as pressure of the test medium acting on the oxygen sensor 106. Measuring the impedances 112, 114, and 122, controlling the operating temperature, and accounting for pressure are essential to accurately operating the oxygen sensor 106. In one embodiment, the computer 102 may determine the impedance 114 of the pump cell 110 by measuring the voltage signal 220 applied to the pump cell 110, illustrated in FIG. 2C, measuring the voltage controlled current 215 directed to the pump cell 110, illustrated in FIG. 2B, and dividing the voltage signal 220 by the voltage controlled current 215. In another embodiment, the computer 102 may determine the impedance 114 of the pump cell 110 by computing a voltage difference between the voltage measurements 233 and 234, or between the voltage measurements 235 and 236, then dividing the voltage difference by the voltage controlled current 215, and then comparing the value with stored tables, formulae, or other similar data supplied by a manufacturer of the oxygen sensor 106. Moreover, the computer 102 may also compare the determined value of the impedance 114 with the manufacturer supplied data to determine a real-time operating temperature of the oxygen sensor 106. In still another embodiment, the impedance 114 may be determined by experimentation. In yet another embodiment, the computer 102 may modulate an electric current directed to a heating element within the oxygen sensor 106 such that a comparison of the impedance 114 and the manufacturer supplied data indicates an appropriate real-time operating temperature of the oxygen sensor 106.

The impedance 112 of the Nernst cell 108 may be determined by way of the reference voltage circuit 126, as well as by controlling the voltage controlled current 215 and the voltage signal 220 directed to the pump cell 110. As illustrated in FIG. 1, one embodiment of the reference voltage circuit 126 comprises a reference voltage source 160, a switch 162 under the control of the computer 102 by way of an electrical connection 164, and a known Nernst cell test impedance 166 which is in electrical communication with the switch 162 and the first terminal 116. During normal operation of the oxygen sensor 106, the computer 102 keeps the switch 162 open, thereby keeping the reference voltage source 160 isolated from the Nernst read circuit 128. When the computer 102 measures the impedance 112, the switch 162 is closed, placing the reference voltage source 160 and the known Nernst cell test impedance 166 into electrical connection with the first terminal 116 of the oxygen sensor 106. Before closing the switch 162, however, the computer 102 prompts the DAC 130 to output a voltage controlled signal 310 to the voltage controlled current source 134.

Figure 3A:
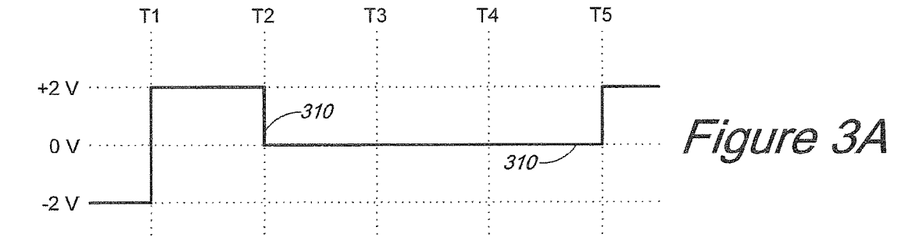
FIG. 3A is a graph illustrating one embodiment of a voltage signal transmitted from a digital-to-analog converter to a voltage controlled current source during measurement of an impedance of a Nernst cell of the present invention.

FIGS. 3A-3E are graphs illustrating one embodiment of the signals arising within the digital control circuit 104 at switch times T1-T5 when the computer 102 is measuring the impedance 112 of the Nernst cell 108. In the illustrated embodiment of FIG. 3A, the voltage controlled signal 310 that is transmitted by the DAC 130 changes from a negative polarity to a positive polarity at switch time T1, remains constant between switch times T1 and T2, and then switches to a value of substantially zero volts at switch time T2. In the embodiment of FIG. 3A, the voltage controlled signal 310 remains at zero volts between the switch time T2 and the switch time T5. At the switch time T5, the voltage-controlled signal 310 changes from zero volts to a positive polarity as the time period for measuring the impedance 112 ends and normal operation of the digital control circuit 104 resumes.

Figure 3B:
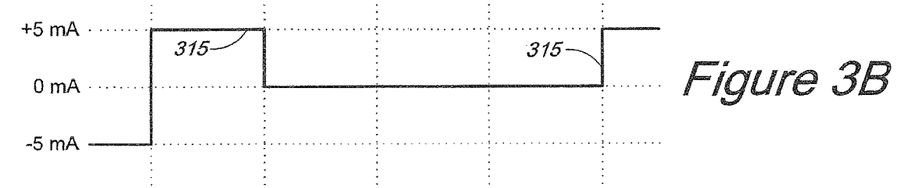
FIG. 3B is a graph illustrating one embodiment of a voltage controlled electric current directed to a pump cell during measurement of an impedance of a Nernst cell of the present invention.
Figures 3C, 3D:
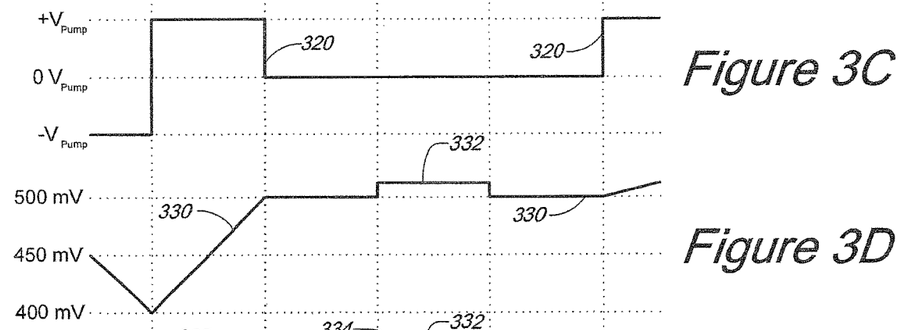
FIG. 3C is a graph illustrating one embodiment of a pump voltage during measurement of an impedance of a Nernst cell in accordance with the present invention.
FIG. 3D illustrates one embodiment of an output voltage signal of a Nernst cell during measurement of an impedance of the Nernst cell in accordance with the present invention.

FIG. 3B is a graph illustrating one embodiment of a voltage controlled electric current 315 which is directed to the pump cell 110 by the voltage controlled current source 134 in response to the voltage controlled signal 310. FIG. 3C is a graph illustrating one embodiment of a pump voltage 320, which is directly proportional to the voltage controlled electric current 315 and the constant reference voltage maintained in the second terminal 118 by the reference voltage 132. The pump voltage 320 and the electric current 315 directed to the pump cell 110 change from negative values to positive values at the switch time T1, remain at constant positive values between the switch times T1 and T2, and then assume values of substantially zero between the switch time T2 and the switch time T5. At switch time T5, the electric current 315 and the pump voltage 320 assume positive values once again as normal operation of the digital control circuit 104 resumes.

Figure 3E:
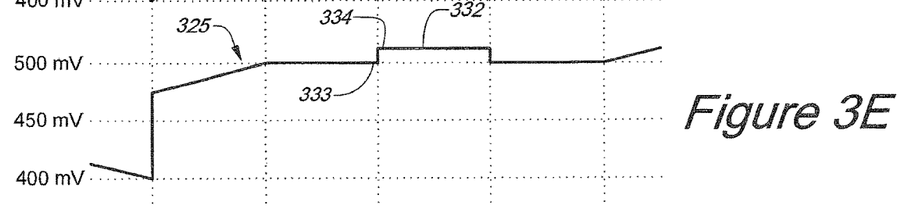
FIG. 3E illustrates one embodiment of an output voltage signal transmitted from an oxygen sensor to a Nernst read circuit during measurement of an impedance of the Nernst cell of the present invention.

During the time period between the switch time T2 and the switch time T5, when the signals within the pump control circuit 124 are substantially zero, the computer 102 uses the electrical connection 164 to close the switch 162. Closing the switch 162 puts the reference voltage source 160 into electrical connection with the known Nernst cell test impedance 166. In one embodiment, the reference voltage source 160 may be connected to an electrical ground of the digital control circuit 104. In other embodiments, the reference voltage source 160 may provide a suitable voltage other than the electrical ground. The voltage due to the reference voltage source 160 and the known Nernst cell test impedance 166 is detectable by way of the first terminal 116 in addition to the voltage due to the Nernst cell 108. FIG. 3D illustrates one embodiment of an output voltage signal 330 of the Nernst cell 108 occurring while the signals within the pump control circuit 124 are zero, as illustrated in FIGS. 3A-3C. FIG. 3E illustrates one embodiment of an output voltage signal 325 which is transmitted from the oxygen sensor 106 to the Nernst read circuit 128 by way of the first terminal 116 and the third terminal 120. In the illustrated embodiment of FIGS. 3D-3E, the reference voltage source 160 and the known Nernst cell test impedance 166 give rise to a voltage step 332 between the switch times T3 and T4.

As illustrated in FIG. 3E, the computer 102 performs a first voltage measurement 333 and a second voltage measurement 334 of the output voltage signal 325. Voltage measurement 333 is performed immediately prior to the switch time T3, before the voltage step 332, and voltage measurement 334 is performed immediately after the switch time T3 during the voltage step 332. The computer 102 may then determine the difference between the first voltage measurement 333 and the second voltage measurement 334, and then use the resulting value in conjunction with the known values of the reference voltage source 160 and the Nernst cell test impedance 166 to calculate a value for the impedance 112. Once the value of the impedance 112 is determined, the computer 102 may compare the value with stored tables, formulae, or other similar data supplied by a manufacturer of the oxygen sensor 106, thereby enabling the computer 102 to determine a current operating temperature of the oxygen sensor 106. In other embodiments, the computer 102 may pass the value of the impedance 112 to a temperature control system (not shown), which may then stabilize the temperature of the oxygen sensor 106 such that the value of the impedance 112 is within a range specified by the manufacturer of the oxygen sensor 106.

After completing the voltage measurements 333, 334, and determining the impedance 112, the digital control circuit 104 may immediately resume normal operation, as depicted by FIGS. 2A-2E. It will be apparent to those skilled in the art that the present invention enables the computer 102 to determine the impedance 112 without utilizing any low-pass filtering of any of the signals within the digital control circuit 104, and thus allows the digital controller 100 to operate at a maximum speed of the oxygen sensor 106. Furthermore, it will be apparent that operating the digital controller 100 at the maximum speed of the oxygen sensor 106 is advantageous in systems wherein the oxygen concentration is in transition, such as during engine load-changes occurring due to vehicle acceleration, deceleration, gear transitions, and the like.

It should be understood that the number of the voltage measurements performed by the computer 102 are not limited to the number shown in FIG. 3E. Rather, the voltage measurements 333 and 334 are merely representative of a spectrum of similar voltage measurements that may be continually performed by the computer 102 for as long as the digital controller 100 is operating. For instance, in another embodiment, voltage measurements may be performed and the impedance 112 determined for each successive cycle of the voltage controlled electric current 215 directed to the pump cell 110, as illustrated in FIG. 2B.

Those skilled in the art will recognize that when the switch 162 is open, the reference voltage source 160 is isolated from the digital control circuit 104. Thus, when the switch 162 is open, the reference voltage source 160 and the known Nernst test impedance 166 have no effect on the output signal 225, illustrated in FIG. 2E. When the switch 162 is closed, however, the reference voltage source 160 and the known Nernst test impedance 166 place a load onto the output signal 225. It will be further recognized by those skilled in the art that with the switch 162 closed, the known Nernst test impedance 166 and the impedance 112 operate as a voltage divider causing attenuation of the output signal 225. In this embodiment, the impedance 112 may be determined by comparing a first amplitude of the output signal 225 when the switch 162 is open to a second amplitude of the output signal 225 when the switch 162 is closed. The computer 102 may determine the difference between the first and second amplitudes and use the value of the known Nernst cell test impedance 166 to calculate the impedance 112. In addition, the computer 102 may also determine the impedance 122 of the third terminal 120. Moreover, the reference voltage source 160 may be decoupled from the known Nernst cell test impedance 166 through a capacitor (not shown), so as to eliminate any interference effects that may arise within the Nernst read circuit 128. It will be appreciated that decoupling the reference voltage source 160 through the capacitor enables this embodiment of the digital control circuit 104 to operate at the maximum speed of the oxygen sensor 106.

As discussed above in connection with FIG. 1, the impedances 112, 114, and 122 are all known to vary with the operating temperature of the oxygen sensor 106. However, the impedances 112 and 114 are also known to vary with pressure of the test medium acting on the oxygen sensor 106, which can cause errors in the output signal 225. Although manufacturers of the oxygen sensor 106 typically provide "correction tables" which can be incorporated into the data stored on the computer 102, a value of the pressure acting on the oxygen sensor 106 must be determined before the correction tables may be utilized. Unlike the impedances 112 and 114, the impedance 122 of the third terminal 120 shows no variation with the pressure acting on the oxygen sensor 106. This distinction enables the computer 102 to compare the impedance 122 with either of the impedances 112 and 114 at a particular operating temperature to determine a relationship between the temperature and the pressure of the test medium on the oxygen sensor 106. Once the relationship between the temperature and pressure on the oxygen sensor 106 is known, the computer 102 may apply the stored manufacturer correction tables so as to obtain more accurate readings from the oxygen sensor 106.

It will be appreciated by those of ordinary skill that determining the pressure of the test medium by way of the impedances 112, 114, and 122 advantageously eliminates any need for an expensive high-temperature gas pressure sensor to be incorporated into the digital controller 100. Moreover, experimentation has shown that when the pressure of the test medium is highly variable, such as in the case of exhaust gases in turbocharged engines, the temperature of the oxygen sensor 106 may be more accurately regulated by measuring the impedance 122 instead of relying on the impedance 112. The impedance 122 may be accurately utilized to regulate the temperature of the oxygen sensor 106 once a relationship between the impedances 112 and 122 has been established at a known temperature and pressure of the test medium.

Figure 4:
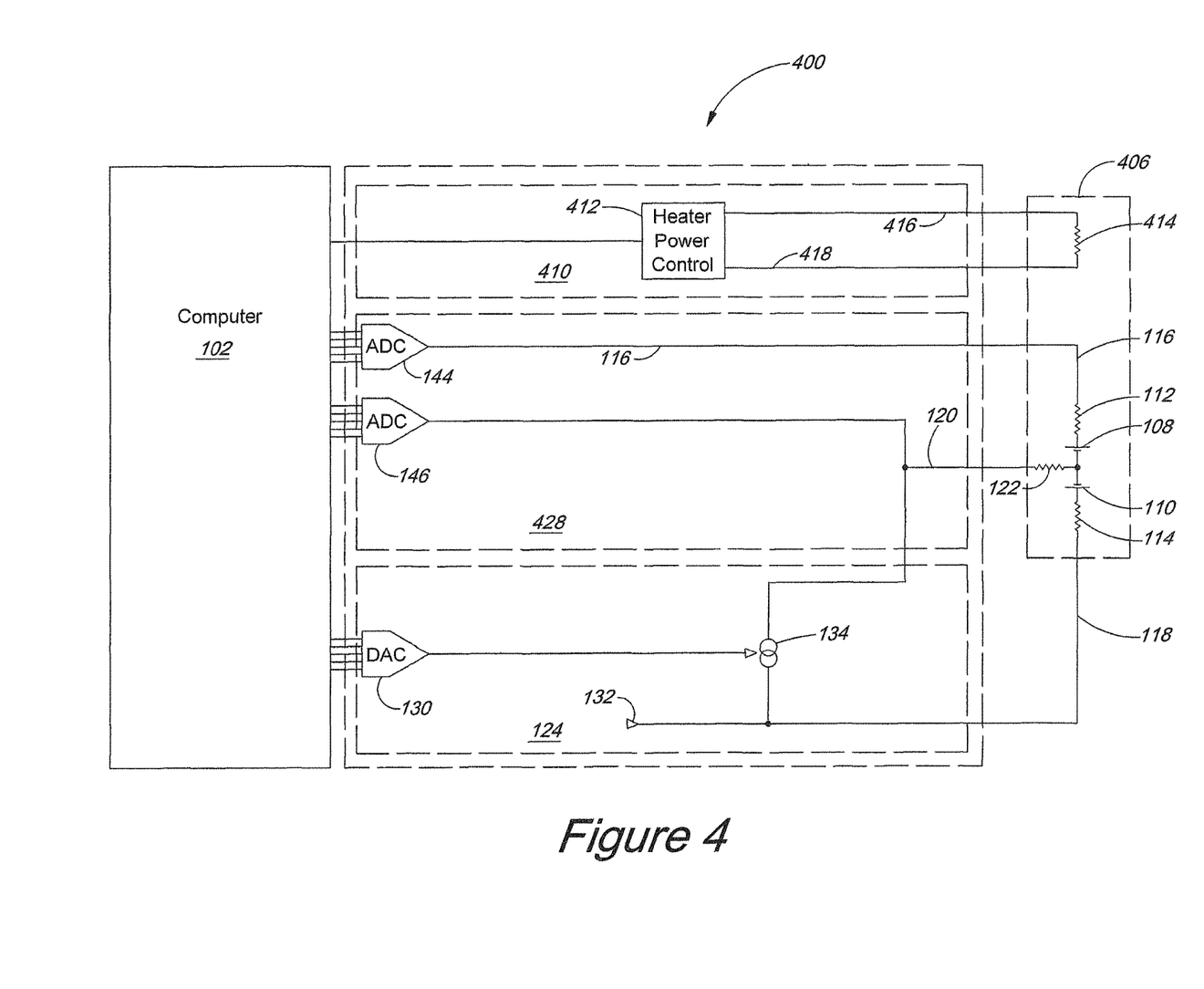
FIG. 4 is a schematic illustration of an embodiment of a temperature-regulating digital controller for an oxygen sensor in accordance with the present invention.

As discussed above in connection with FIG. 1, various components of the Nernst read circuit 128 may be advantageously combined. Combing the components illustrated in FIG. 1 reduces the complexity of the digital control circuit 104, decreases manufacturing costs, and potentially improves the speed and accuracy of oxygen concentration readings. FIG. 4 is a schematic illustration of an embodiment of a temperature-regulating digital controller 400 for an oxygen sensor 406. The oxygen sensor 406 is substantially identical to the oxygen sensor 106 with the exception that the oxygen sensor 406 comprises a heating element 414. The temperature-regulating digital controller 400 comprises the pump control circuit 124, a temperature control circuit 410, and a Nernst read circuit 428. Although the Nernst read circuit 428 operates substantially the same as the Nernst read circuit 128; in the Nernst read circuit 428, the signal amplifiers 136, 138, the sample-and-hold circuits 140, 142, and the electrical connections 156, 158 are incorporated into the ADCs 144, 146. In another embodiment, suitable ADCs 144, 146 may be selected for use in the Nernst read circuit 428 such that the signal amplifiers 136, 138, the sample-and-hold circuits 140, 142, and the electrical connections 156, 158 may be omitted altogether.

Figure 5:
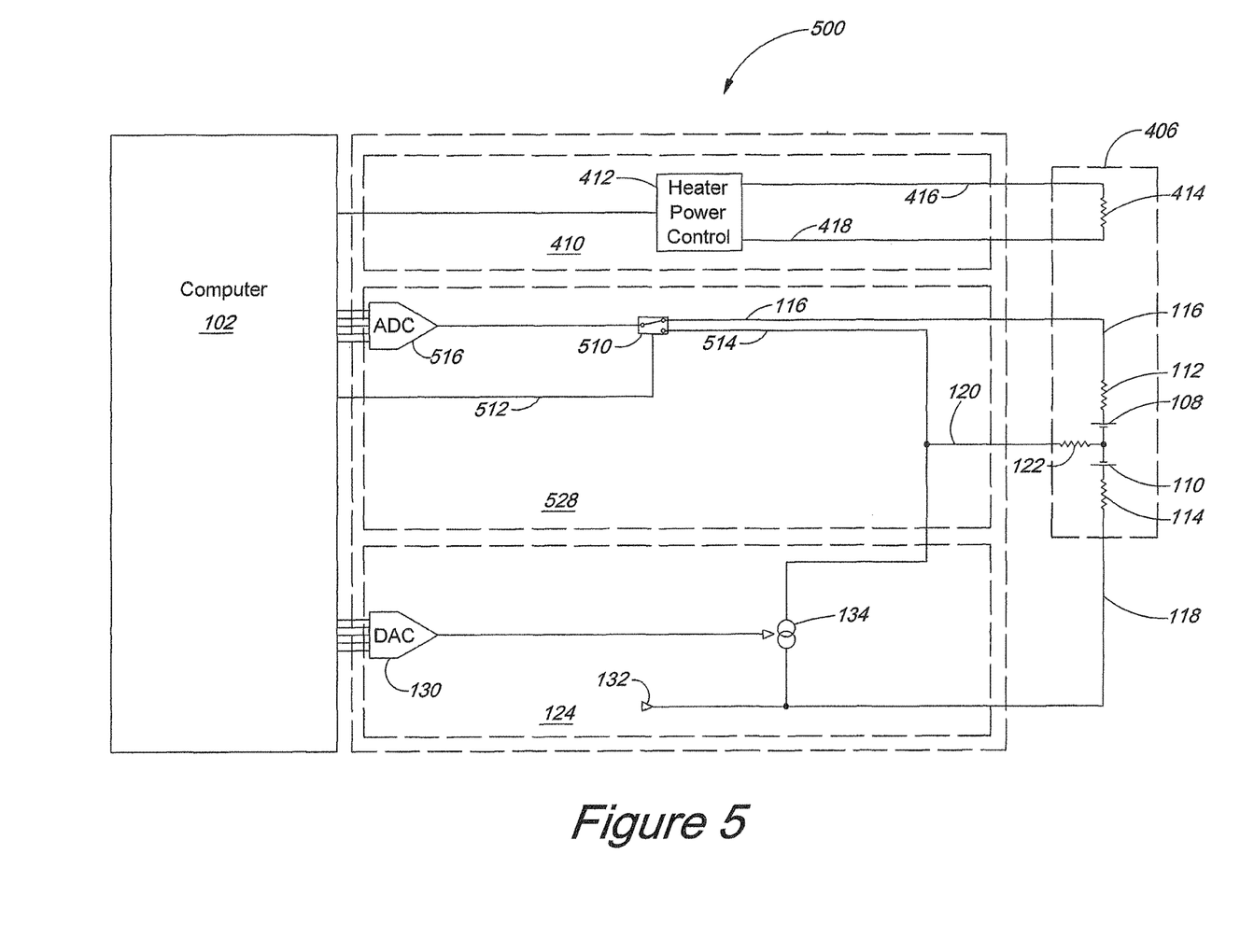
FIG. 5 is a schematic illustration of an embodiment of a temperature-regulating digital controller for an oxygen sensor in accordance with the present invention.

FIG. 5 is a schematic illustration of one embodiment of a temperature-regulating digital controller 500 for the oxygen sensor 406. Similar to the temperature-regulating digital controller 400, the temperature-regulating digital controller 500 comprises the pump control circuit 124, the temperature control circuit 410, and a Nernst read circuit 528. In the illustrated embodiment of FIG. 5, the Nernst read circuit 528 comprises a switch 510 in operative communication with the computer 102 by way of an electrical connection 512, an electrical connection 514 which is connected to the third terminal 120, and an ADC 516. Those skilled in the art will recognize that the ADC 516 may be placed into electrical communication with either the first terminal 116 or the third terminal 120 of the oxygen sensor 406 according to signals transmitted from the computer 102 to the switch 510 by way of the electrical connection 512. Thus, the ADC 516 may perform substantially the same functions as both of the ADCs 144, 146.

The temperature control circuit 410, illustrated in FIGS. 4-5, comprises a heater power control 412 in operative communication with the computer 102, and the heating element 414. The heating element 414 is electrically connected to a fourth terminal 416 and a fifth terminal 418 of the oxygen sensor 406. The fourth terminal 416 and the fifth terminal 418 enable the heater power control 412 to direct an electric current to the heating element 414 so as to control the temperature of the oxygen sensor 406 according to signals received from the computer 102.

During operation of the temperature-regulating digital controllers 400, 500, the pump control circuit 124 functions as discussed in connection with FIGS. 2A-2C. Likewise, the Nernst cell 108, the pump cell 110, and the impedances 112, 114, and 122 all behave as discussed with reference to FIGS. 2A-2E. However, experimentation has demonstrated that while the pump cell 110 operates under the action of the voltage controlled electric current 215, a voltage contribution to the output signal 225 due to the pump cell 110 is measurable at the first terminal 116 and the third terminal 120. In practice, the voltage contribution due to the pump cell 110 may be resolved by computing a voltage difference between the voltage measurements 233 and 234, or alternatively between the voltage measurements 235 and 236. The impedance 114 of the pump cell 110 may then be determined in real-time by dividing the voltage difference by the electric current 215 directed to the pump cell. In the embodiments illustrated in FIGS. 4-5, the impedance 114 may be determined by the computer 102 in accordance with stored data, tables, formulae, or other similar information. Experimentation has demonstrated that using the voltage measurements 233, 234, 235, and 236 provides values for the impedance 114 that are free of any contribution due to the impedance 122.

It will be appreciated by those skilled in the art that since the impedance 114 is sensitive to the operating temperature of the oxygen sensor 406, the impedance 114 may be used to regulate the sensor's temperature in real time. In the illustrated embodiments of FIGS. 4-5, the computer 102 may determine a real-time value of the impedance 114, as described above, and then perform a comparison of the real-time value with known impedance values that are stored on the computer 102. The known impedance values may be manufacturer-specified values, or may be a manufacturer-specified range of impedance values. The comparison may be based on manufacturer supplied data, tables, formulae, or other similar information relating the impedance 114 to the operating temperature of the oxygen sensor 406.

In one embodiment, the computer 102 may signal the heater power control 412 to direct an electric current to the heating element 414 by way of the fourth terminal 416 and the fifth terminal 418 so as to control the temperature of the oxygen sensor 406. In another embodiment, the computer 102 may signal the heater power control 412 to modulate the electric current directed to the heating element 414. The computer 102 may continue signaling the heater power control 412 and performing the comparison of real-time impedance values with the known impedance values until the comparison indicates that the oxygen sensor 406 is operating at an appropriate temperature. It will be appreciated that the since the computer 102 continually receives the voltage contribution due to the pump cell 110 with the voltage measurements 233, 234, 235, and 236, the computer 102 may continually signal the heater power control 412 to modulate the electric current directed to the heating element 414, and thereby continually regulate the operating temperature of the oxygen sensor 406.

Those of ordinary skill in the art will appreciate that regulating the operating temperature of the oxygen sensor 406 by way of the impedance 114 eliminates any need for signal filtering circuitry, thereby enabling the temperature-regulated digital controllers 400, 500 to operate at the maximum speed of the oxygen sensor 406. In one embodiment, the heater power control 412 may modulate the electric current directed to the heating element 414 with a high frequency without any need for additional signal filtering circuitry. In another embodiment, the electric current may be modulated with a frequency that is substantially equal to the maximum frequency of operation of the pump cell 110. In another embodiment, the electric current may be modulated with a frequency of substantially 32 kHz. In still another embodiment, the fourth terminal 416 may include an inductor which operates to make the modulated current to the heating element resemble a direct current (DC), thereby reducing any interference that may be induced in other portions of the digital controllers 400, 500. In yet other embodiments, the inductor in the fourth terminal 416 may be suitably coupled with diodes, capacitors, and other well known components, to further reduce signal interference effects that may be induced by the heating element 414. It will be readily apparent to those of ordinary skill that a variety of components and circuits may be employed to reduce, or substantially eliminate, signal interference in other portions of the digital controllers 400, 500 without deviating from the spirit and scope of the present invention.

While some specific embodiments of the invention have been shown the invention is not to be limited to these embodiments. For example, most functions performed by electronic hardware components may be duplicated by software emulation. Thus, a software program written to accomplish those same functions may emulate the functionality of the hardware components in input-output circuitry. The invention is to be understood as not limited by the specific embodiments described herein, but only by scope of the appended claims.

The invention claimed is:

1. An apparatus for detecting a difference in oxygen content in a test medium relative to a reference medium, comprising:
   a computer configured to send and receive digital signals so as to communicate with and operate circuitry comprising said apparatus;
   an oxygen sensor comprising at least one Nernst cell and a pump cell, wherein the oxygen sensor is configured to electrically indicate the difference in oxygen content in the test medium relative to the reference medium;
   a pump control circuit configured to operate the pump cell according to signals received from the computer;

a reference voltage circuit configured to determine an impedance of the oxygen sensor according to signals received from the computer;

a Nernst read circuit configured to amplify output signals from the oxygen sensor via at least one signal amplifier, and transmit the signals digitally to the computer via at least one analog-to-digital converter, wherein the signals received by the computer are compared with stored reference information to determine the oxygen content of the test medium; and wherein a first terminal of the oxygen sensor is electrically connected to the Nernst cell, a second terminal of the oxygen sensor is electrically connected to the pump cell, and a third terminal of the oxygen sensor is electrically common to both the Nernst cell and the pump cell.

2. The apparatus of claim 1, wherein the test medium is exhaust gases from an internal combustion engine.

3. The apparatus of claim 2, wherein the reference medium is a sealed gas charge, surrounding atmospheric air, or a functional equivalent.

4. The apparatus of claim 1, wherein the pump control circuit further comprises a digital-to-analog converter in operative communication with the computer, a reference voltage source, and a voltage controlled current source, where the reference voltage source is electrically connected to the second terminal and the voltage controlled current source, and the voltage controlled current source is electrically connected to the third electrical terminal.

5. The apparatus of claim 1, wherein the Nernst read circuit is in operative communication with the computer through at least one analog-to-digital converter.

6. The apparatus of claim 1, wherein said computer further includes stored reference information to determine the oxygen content of the test medium based on signals received from the Nernst read circuit.

7. An apparatus for detecting a difference in oxygen content in a test medium relative to a reference medium, comprising:

a computer configured to send and receive digital signals so as to communicate with and operate circuitry comprising said apparatus, wherein said computer further includes stored reference information to determine the oxygen content of the test medium;

an oxygen sensor comprising at least one Nernst cell and a pump cell, wherein a first terminal of the oxygen sensor is electrically connected to the Nernst cell, a second terminal of the oxygen sensor is electrically connected to the pump cell, and a third terminal of the oxygen sensor is electrically common to both the Nernst cell and the pump cell;

a pump control circuit comprising a digital-to-analog converter in operative communication with the computer, a reference voltage source, and a voltage controlled current source, where the reference voltage source is electrically connected to the second terminal and the voltage controlled current source, and the voltage controlled current source is electrically connected to the third electrical terminal;

a reference voltage circuit comprising a reference voltage source, a switch in operative communication with the computer, and a known Nernst cell test resistance, where the known Nernst cell test resistance is connected to the first electrical terminal of the oxygen sensor; and a Nernst read circuit comprising at least one signal amplifier configured to amplify output signals from the oxygen sensor, and at least one analog-to-digital converter in operative communication with the at least one Nernst cell and the computer, wherein the at least one signal amplifier is incorporated into the at least one analog-to-digital converter.

8. The apparatus of claim 7, wherein at least one switch is operated by the computer such that an output voltage signal of the Nernst cell is passed to the at least one analog-to-digital converter and interpreted by the computer.

9. The apparatus of claim 7, wherein the test medium is exhaust gases from an internal combustion engine.

10. The apparatus of claim 9, wherein the reference medium is a sealed gas charge, surrounding atmospheric air, or a functional equivalent.

11. A method for detecting a difference in oxygen content in a test medium relative to a reference medium, comprising:

configuring a computer to send and receive digital signals so as to communicate with and operate circuitry suitable for detecting the difference in oxygen content in the test medium relative to the reference medium;

using an oxygen sensor comprising at least one Nernst cell, a pump cell, and a heating element to electrically indicate the difference in oxygen content in the test medium relative to the reference medium, wherein a first terminal is electrically connected to the Nernst cell, a second terminal is electrically connected to the pump cell, and a third terminal of the oxygen sensor is electrically common to both the Nernst cell and the pump cell;

operating the pump cell according to signals received from the Nernst cell;

determining a real-time impedance of the Nernst cell;

determining a real-time impedance of the third terminal of the oxygen sensor;

determining a pressure of the test medium acting on the oxygen sensor;

regulating a temperature of the oxygen sensor;

transmitting output signals from the Nernst cell digitally to the computer via at least one analog-to-digital converter suitable for transmitting output signals without amplification; and comparing the output signals received from the Nernst cell with stored reference information to determine the oxygen content of the test medium.

12. The method of claim 11, wherein operating the pump cell further comprises using a reference voltage source to maintain the second terminal at a constant reference voltage, and using a digital-to-analog converter in communication with the computer to operate a voltage controlled current source, where the voltage controlled current source directs an electric current to the third electrical terminal of the oxygen sensor according to the output signals received from the Nernst cell.

13. The method of claim 12, wherein operating the pump cell further comprises varying the electric current directed to the third electrical terminal such that the output signals received from the Nernst cell indicate a steady voltage of 450 mV.

14. The method of claim 13, wherein determining a real-time impedance of the Nernst cell comprises performing at least a first measurement and a second measurement of the output signals received from the Nernst cell at the first terminal, wherein the first measurement is performed while directing zero electric current to the third terminal and the second measurement is performed while using a reference voltage circuit to apply a known reference voltage to a known Nernst cell test resistance, and using the difference between the first measurement and the second measurement in conjunction with the known reference voltage and the known Nernst cell test resistance to resolve the real-time impedance of the Nernst cell.

15. The method of claim 14, further comprising successively performing the first measurement and the second measurement whenever zero electric current is directed to the third terminal, where the known reference voltage is decoupled through a capacitor after each of the second measurements such that the Nernst cell indicates a steady output voltage.

16. The method of claim 15, wherein determining a real-time impedance of the third terminal of the oxygen sensor comprises measuring electric signals in the first terminal, the second terminal, and the third terminal, and discerning the real-time impedance of the third terminal based on relative amplitudes of the electric signals.

17. The method of claim 16, wherein determining a pressure of the test medium acting on the oxygen sensor comprises establishing a relationship between the real-time impedance of the third terminal of the oxygen sensor with the real-time impedance of the Nernst cell and a real-time impedance of the pump cell, wherein the impedance of the Nernst cell and the impedance of the pump cell change in proportion to the temperature of the oxygen sensor and the pressure of the test medium, and wherein the impedance of the third terminal of the oxygen sensor is insensitive to the pressure of the test medium.

18. The method of claim 11, wherein transmitting output signals comprises passing an output voltage of the Nernst cell to the at least one analog-to-digital converter for interpretation by the computer.

19. The method of claim 11, wherein the test medium is exhaust gases from an internal combustion engine.

20. The method of claim 19, wherein the reference medium is a sealed gas charge, surrounding atmospheric air, or a functional equivalent.

21. The method of claim 11, wherein regulating the temperature comprises:
measuring a voltage contribution of the pump cell arising between the first terminal and the third terminal;
determining a pump cell impedance in accordance with the voltage contribution and the electric current directed to the pump cell;
deducing a real-time temperature of the oxygen sensor by comparing the pump cell impedance with known impedance values, wherein the pump cell impedance changes in proportion to the temperature of the oxygen sensor; and
modulating an electric current directed to the heating element such that a comparison of the pump cell impedance and the known impedance values indicates an appropriate operating temperature of the oxygen sensor.

22. An apparatus for detecting a difference in oxygen content in a test medium relative to a reference medium, comprising:
a computer configured to send and receive digital signals so as to communicate with and operate circuitry comprising said apparatus;
an oxygen sensor comprising at least one Nernst cell, a pump cell, and a heating element, wherein the oxygen sensor is configured to electrically indicate the difference in oxygen content in the test medium relative to the reference medium;
a pump control circuit configured to operate the pump cell according to signals received from the computer;
a temperature control circuit configured to regulate an operating temperature of the oxygen sensor according to signals received from the computer; and
a Nernst read circuit, comprising at least one analog-to-digital converter, configured to amplify and transmit output signals from the oxygen sensor digitally to the computer, wherein the signals received by the computer are compared with stored reference information to determine the oxygen content of the test medium.

23. The apparatus of claim 22, wherein a first terminal of the oxygen sensor is electrically connected to the Nernst cell, a second terminal of the oxygen sensor is electrically connected to the pump cell, a third terminal of the oxygen sensor is electrically common to both the Nernst cell and the pump cell, a fourth terminal of the oxygen sensor is electrically connected to a first input of the heating element, and a fifth terminal of the oxygen sensor is electrically connected to a second input of the heating element.

24. The apparatus of claim 22, wherein the pump control circuit further comprises a digital-to-analog converter in operative communication with the computer, a reference voltage source, and a voltage controlled current source, where the reference voltage source is electrically connected to the second terminal and the voltage controlled current source, and the voltage controlled current source is electrically connected to the third electrical terminal.

25. The apparatus of claim 22, wherein the temperature control circuit further comprises a heater power control in operative communication with the computer, wherein the heater power control is connected to the fourth terminal and the fifth terminal of the oxygen sensor.

26. The apparatus of claim 25, wherein the heater power control is configured to regulate the temperature of the oxygen sensor by directing a current to the heating element according to signals received from the computer.

27. A method for regulating an operating temperature of a digitally controlled oxygen sensor, comprising:
measuring a voltage contribution of a pump cell of the oxygen sensor arising between a first terminal and a second terminal of a Nernst cell of the oxygen sensor;
determining a pump cell impedance in accordance with the voltage contribution and an electric current directed to the pump cell;
converting, via an analog-to-digital converter, the determined pump cell impedance into a digital form for comparison;
deducing a real-time temperature of the oxygen sensor by digitally comparing the pump cell impedance with known impedance values, wherein the pump cell impedance changes in proportion to the temperature of the oxygen sensor; and
modulating an electric current directed to a heating element of the oxygen sensor such that a comparison of the pump cell impedance and the known impedance values indicates an appropriate operating temperature of the oxygen sensor.

28. An apparatus for detecting a difference in oxygen content in a test medium relative to a reference medium, comprising:
a computer configured to send and receive digital signals so as to communicate with and operate circuitry comprising said apparatus;
an oxygen sensor comprising at least one Nernst cell and a pump cell, wherein the oxygen sensor is configured to electrically indicate the difference in oxygen content in the test medium relative to the reference medium;

a pump control circuit configured to operate the pump cell according to signals received from the computer;

a reference voltage circuit configured to determine an impedance of the oxygen sensor according to signals received from the computer comprising a reference voltage source, a switch in operative communication with the computer, and a known Nernst cell test resistance, where the known Nernst cell test resistance is connected to the first electrical terminal of the oxygen sensor; and a Nernst read circuit configured to amplify output signals from the oxygen sensor via at least one signal amplifier, and transmit the signals digitally to the computer via at least one analog-to-digital converter, wherein the signals received by the computer are compared with stored reference information to determine the oxygen content of the test medium.

29. An apparatus for detecting a difference in oxygen content in a test medium relative to a reference medium, comprising:

a computer configured to send and receive digital signals so as to communicate with and operate circuitry comprising said apparatus;

an oxygen sensor comprising at least one Nernst cell and a pump cell, wherein the oxygen sensor is configured to electrically indicate the difference in oxygen content in the test medium relative to the reference medium;

a pump control circuit configured to operate the pump cell according to signals received from the computer;

a reference voltage circuit configured to determine an impedance of the oxygen sensor according to signals received from the computer; and a Nernst read circuit in operative communication with the computer configured to amplify output signals from the oxygen sensor via at least one signal amplifier, and transmit the signals digitally to the computer via at least one analog-to-digital converter, wherein the signals received by the computer are compared with stored reference information to determine the oxygen content of the test medium; and wherein at least one switch is operated by the computer such that an output voltage signal of the Nernst cell is passed to the at least one analog-to-digital converter and interpreted by the computer.

30. An apparatus for detecting a difference in oxygen content in a test medium relative to a reference medium, comprising:

a computer configured to send and receive digital signals so as to communicate with and operate circuitry comprising said apparatus;

an oxygen sensor comprising at least one Nernst cell and a pump cell, wherein the oxygen sensor is configured to electrically indicate the difference in oxygen content in the test medium relative to the reference medium and wherein the impedance of the oxygen sensor varies in proportion to temperature;

a pump control circuit configured to operate the pump cell according to signals received from the computer;

a reference voltage circuit configured to determine an impedance of the oxygen sensor according to signals received from the computer; and a Nernst read circuit configured to amplify output signals from the oxygen sensor via at least one signal amplifier, and transmit the signals digitally to the computer via at least one analog-to-digital converter, wherein the signals received by the computer are compared with stored reference information to determine the oxygen content of the test medium.

* * * * *